United States Patent
Wulff-Döring et al.

[11] Patent Number: 6,162,928
[45] Date of Patent: Dec. 19, 2000

[54] PREPARATION OF PYRROLES

[75] Inventors: Joachim Wulff-Döring, Frankenthal; Joachim Simon, Mannheim; Michael Hesse, Worms; Peter Wahl, Ladenburg, all of Germany

[73] Assignee: BASF Aktiengesellschaft, Ludwigshafen, Germany

[21] Appl. No.: 09/553,254

[22] Filed: Apr. 20, 2000

[30] Foreign Application Priority Data

Apr. 23, 1999 [DE] Germany .......................... 199 18 568

[51] Int. Cl.$^7$ .............................................. C07D 207/323
[52] U.S. Cl. ................................................ 548/564
[58] Field of Search ............................................. 548/564

[56] References Cited

U.S. PATENT DOCUMENTS

| | | | |
|---|---|---|---|
| 3,522,269 | 7/1970 | Guyer | 260/313.1 |
| 4,762,929 | 8/1988 | Rebafka | 546/252 |

FOREIGN PATENT DOCUMENTS

| | | |
|---|---|---|
| 67 360 | 12/1982 | European Pat. Off. . |
| 155 649 | 9/1985 | European Pat. Off. . |
| 1 393 086 | 5/1975 | United Kingdom . |

*Primary Examiner*—Laura L. Stockton
*Attorney, Agent, or Firm*—Keil & Weinkauf

[57] ABSTRACT

A process for preparing pyrroles of the formula I:

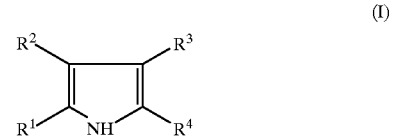

(I)

where $R_1$, $R^2$, $R^3$ and $R^4$ are identical or different and are hydrogen atoms, alkyl groups having from 1 to 12 carbon atoms or cycloalkyl groups having from 3 to 12 carbon atoms, by dehydrogenation of pyrrolidines of the formula II:

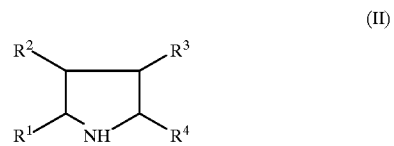

(II)

where $R^1$, $R^2$, $R^3$ and $R^4$ are as defined above, in the presence of a supported noble metal catalyst is described. In this process, the dehydrogenation is carried out at from 150 to 300° C. and pressures of from 0.01 to 50 bar and the noble metal catalyst comprises from 30 to 100% by weight of:
  a) palladium on an oxide of a rare earth or an oxide of an element of the 4$^{th}$ group (transition group IV) of the Periodic Table, or
  b) a platinum/palladium mixture on aluminum oxide, an oxide of a rare earth or an oxide of an element of the 4$^{th}$ group and from 0 to 70% by weight of alkali metal oxide or alkaline earth metal oxide.

8 Claims, No Drawings

PREPARATION OF PYRROLES

The present invention relates to a process for preparing pyrroles from pyrrolidine or substituted pyrrolidines by dehydrogenation over noble metal catalysts.

Hitherto, it has been essentially Pd catalysts which have been used in the preparation of pyrrole and substituted pyrroles from the corresponding pyrrolidines. These catalysts have a relatively low activity.

U.S. Pat. No. 3 522 269 describes the dehydrogenation of pyrrolidine to pyrrole over Pd catalysts at very high temperatures (preferably 400–450° C.), with the catalysts becoming deactivated relatively quickly.

GB-A 1 393 086 describes the dehydrogenation of piperidine to pyridine by means of catalysts comprising palladium on $SiO_2$ as support. The catalysts are produced in halogenated hydrocarbons, i.e. under conditions which pollute the environment.

EP-A 67 360 and 155 649 describe Pd catalysts for the dehydrogenation of pyrrolidines; these catalysts are effective at relatively low temperatures, but also display a comparatively low activity.

It is an object of the present invention to propose a process for the catalytic dehydrogenation of pyrrolidine or substituted pyrrolidines to give the corresponding pyrroles and also a catalyst for this process, which ensure high effectiveness over a prolonged period and make it possible to work in an environmentally friendly manner.

The invention starts out from a process for preparing pyrroles of the formula I:

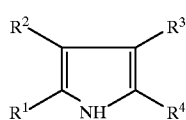

where $R^1$, $R^2$, $R^3$ and $R^4$ are identical or different and are hydrogen atoms, alkyl groups having from 1 to 12 carbon atoms or cycloalkyl groups having from 3 to 12 carbon atoms, by dehydrogenation of pyrrolidines of the formula II:

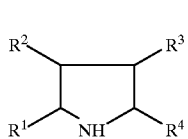

where $R^1$, $R^2$, $R^3$ and $R^4$ are as defined above, in the presence of a supported noble metal catalyst.

In the process of the present invention, the dehydrogenation is carried out at from 150 to 300° C. and pressures of from 0.01 to 50 bar and the noble metal catalyst comprises from 30 to 100% by weight of:
 a) palladium on an oxide of a rare earth or an oxide of an element of the $4^{th}$ group (transition group IV) or
 b) a platinum/palladium mixture on aluminum oxide, an oxide of a rare earth or an oxide of an element of the $4^{th}$ group and from 0 to 70% by weight of alkali metal oxide or alkaline earth metal oxide.

The process of the present invention can be carried out as follows:

The conversion of the pyrrolidines of the formula II into the pyrroles I can be carried out over a heterogeneous catalyst in the liquid phase or preferably in the gas phase at from 150 to 300° C., preferably from 170 to 270° C., particularly preferably from 180 to 250° C., and pressures of from 0.01 to 50 bar, preferably from 0.1 to 5 bar, particularly preferably from 1 to 1.5 bar.

Nitrogen and hydrogen are generally used in a molar ratio to the pyrrolidine used of from 1:1 to 100:1, preferably from 2:1 to 50:1, particularly preferably from 3:1 to 40:1. The molar ratio of nitrogen to hydrogen can be from 0.01:1 to 100:1, preferably from 0.1:1 to 10:1, particularly preferably from 0.5:1 to 5:1.

The reaction is preferably carried out in a tube reactor, since it is important to avoid backmixing from the outlet from the plant, i.e. the end of the last reaction zone, to the inlet, i.e. the beginning of the first reaction zone, which can most easily be achieved in tube reactors and by means of the plug flow occurring therein.

The catalyst can be located in a fixed bed or in a fluidized bed. The heterogeneous catalysts of the present invention have been found to be useful as tailor-made catalysts for the second reaction zone.

Suitable heterogeneous catalysts comprise from 30 to 100% by weight, preferably from 50 to 100% by weight, particularly preferably from 70 to 100% by weight, of:
 a) palladium on an oxide of a rare earth or an oxide of an element of the $4^{th}$ group (transition group IV) of the Periodic Table or
 b) a platinum/palladium mixture on aluminum oxide, an oxide of a rare earth or an oxide of an element of the $4_{th}$ group and from 0 to 70% by weight, preferably from 0 to 50% by weight, particularly preferably from 0 to 30% by weight, of an alkali metal oxide and/or alkaline earth metal oxide.

Rare earths for the purposes of the present description are the elements of the lanthanide and actinide groups of the Periodic Table, e.g. lanthanum, cerium, neodymium, samarium, gadolinium, ytterbium, actinium, thorium, uranium and neptunium, preferably cerium, praseodymium, neodymium, samarium, europium, terbium, ytterbium, thorium and protactinium, particularly preferably cerium, praseodymium, neodymium and thorium.

Suitable metals of the $4^{th}$ group are, inter alia, titanium, zirconium and hafnium, preferably titanium and zirconium, particularly preferably zirconium.

Examples of suitable alkali metals and alkaline earth metals are lithium, sodium, potassium, cesium, beryllium, magnesium, calcium, strontium and barium, preferably sodium, potassium, magnesium, calcium and barium.

The active constituents of the catalyst (noble metals) are, in the case of pure palladium, preferably present on oxides of the lanthanides or actinides or on oxides of elements of the $4^{th}$ group, and, in the case of platinum/palladium mixtures, preferably present on supports consisting essentially of aluminum oxide. on oxides of the rare earths or on oxides of the $4^{th}$ group.

If additives (i.e. alkali metal oxides or alkaline earth metal oxides) are present, the catalysts can be prepared by compounding of the additives together with the support material, thermal after-treatment (heat treatment) at from 400 to 900° C. and impregnation with a solution comprising a salt of the noble metal or by impregnation of the support with a solution of additives and of the noble metal, e.g. in the form of solutions of their nitrates, chlorides, formates, oxalates or ammonia complexes and subsequent heat treatment at from 400 to 900° C. If spinel formation is to be effected, a temperature of from 900 to 1300° C. has to be achieved after compounding or impregnation of the aluminum oxide with the oxide or solution of the additive component (see Ullmanns Encyklopadie der technischen Chemie, 3$^{rd}$ edition (1955), Volume 6, pages 242 to 244).

The noble metal content of the catalyst, based on the support material, is generally from 0.0001 to 25% by weight, preferably from 0.001 to 20% by weight, particularly preferably from 0.05 to 15% by weight. The catalysts can be used, for example, in the form of shaped bodies, e.g. extrudates, pellets or rings, or as powder, depending on the intended application.

Compared to the known processes, the process of the present invention has the advantage that the use of catalysts which are more active and deactivate more slowly in the dehydrogenation results in significantly fewer interruptions or downtimes being required for changing the catalyst in industrial operation and therefore results in an increase in capacity. Furthermore, the catalysts used according to the present invention have a higher initial selectivity for the synthesis of aromatic heterocycles, so that the selectivity is significantly better over the entire running time with one catalyst charge.

The formation of frequently occurring typical by-products such as pyrrolines, etc., can be largely suppressed in the process of the present invention so that only small amounts, if any, of these by-products are formed.

The substituents $R^1$, $R^2$, $R^3$, $R^4$ and $R^5$ in the formulae I and II have the following meanings:

hydrogen, $C_1$–$C_{12}$-alkyl, preferably $C_1$–$C_8$-alkyl, particularly preferably $C_1$–$C_4$-alkyl. e.g. methyl, ethyl, isopropyl, n-butyl, sec-butyl and tert-butyl, $C_3$–$C_{12}$-cycloalkyl, preferably $C_5$–$C_8$-cycloalkyl, particularly preferably $C_5$- or $C_6$-cycloalkyl, where these radicals may, if desired, be substituted by from 1 to 3 substituents such as halogen atoms or $C_1$–$C_4$-alkyl groups.

extrudates. The extrudates were then dried at 120° C. for 4 hours and then calcined at 520° C. for 2 hours.

The catalyst A produced in this way in accordance with EP-A 167 996 contained 1% by weight of Pd on a support consisting of 19.4% by weight of magnesium oxide and 80.6% by weight of aluminum oxide.

An electrically heatable 2.5 l capacity tube reactor having a length of 1 m was charged with 750 ml of catalyst. The reactor was then heated to 180° C. (5° C. per minute) while passing a stream of nitrogen (100 l per hour) through it and was held at this temperature. Over the next 4 hours, 30 l of hydrogen per hour were metered in. Subsequently, the nitrogen was gradually replaced by hydrogen over a period of 4 hours until only hydrogen was being passed through the reactor. The temperature was then firstly brought to 200° C., held at this level for 2 hours, subsequently increased to 220° C. and again held at this level for 2 hours. The activated catalyst was used directly for the experiment and kept under nitrogen until the beginning of the experiment.

The reaction was carried out under atmospheric pressure in a gas stream (100 standard liters per hour of nitrogen, 30 standard liters per hour of hydrogen). 0.06 kg of feed (pyrrolidine vapor) per liter of catalyst per hour was metered via a vaporizer into the gas stream. Downstream of the reactor, the liquid reaction products were condensed by means of a two-stage intensive cooler with downstream cold trap and were analyzed by gas chromatography. At the end of the day, the reactor was flushed with ammonia/hydrogen for another 1 hour and finally cooled under nitrogen.

The experimental results are summarized in Table 1 below.

TABLE 1

| Run time (hours) | Temp. (° C.) | Feed (g) | Output (g) | Pyrroline | Pyrrolidine (area-% in GC) | Pyrrole | Others | Conversion % | Sel. % |
| --- | --- | --- | --- | --- | --- | --- | --- | --- | --- |
| Catalyst A: | | | | | | | | | |
| 7 | 230 | 298 | 200 | 2.0 | 4.8 | 70.9 | 22.3 | 95.2 | 74.5 |
| 14 | 230 | 298 | 251 | 8.2 | 21.0 | 56.4 | 14.4 | 79.0 | 71.4 |
| 21 | 240 | 298 | 248 | 9.0 | 16.6 | 59.4 | 15.1 | 83.4 | 71.2 |
| 25 | 240 | 185 | 150 | 4.3 | 13.0 | 65.0 | 17.9 | 87.0 | 74.7 |
| 32 | 240 | 298 | 249 | 10.7 | 24.2 | 53.0 | 12.1 | 75.8 | 69.9 |
| Mean: | 236 | 275 | 220 | 6.8 ± 3.6 | 15.9 ± 7.5 | 60.9 ± 7.1 | 16.4 ± 3.9 | 84.1 ± 7.5 | 72.3 ± 2.1 |

The compounds prepared by the process of the invention can be used, for example, for preparing pharmaceutical active compounds and are valuable intermediates for the synthesis thereof.

EXAMPLE 1

Comparative example in accordance with EP-A 67 360:

8 kg of aluminum oxide were compounded with 2 kg of magnesium oxide (in each case calculated as pure $Al_2O_3$ and MgO) with addition of about 10 liters of water and subsequently extruded to give 4 mm thick extrudates. The extrudates obtained were dried at 120° C. for 6 hours and then heat-treated at 450° C. for 2 hours.

The extrudates were impregnated with a palladium nitrate solution having a concentration of 5% by weight in an impregnation drum by spraying the solution hot onto the Sel. denotes selectivity, i.e yield of pyrrole based on pyrrolidine reacted. The yield were determined by gas chromatography and reported in percent by area. During the experiment, the temperature had to be increased to maintain the activity level, i.e. the activity at constant temperature decreased.

EXAMPLE 2

The procedure of Example 1 was repeated, but using catalyst B in place of catalyst A. Catalyst B was produced by a method analogous to that for catalyst A, but $ZrO_2$ extrudates were used as support and the palladium nitrate solution was replaced by a solution comprising equal amounts of palladium nitrate and platinum nitrate. The catalyst produced in this way contained 0.5% by weight of Pt and 0.5% by weight of Pd.

The experimental result are summarized in Table 2 below.

TABLE 2

| Run time (hours) | Temp. (°C.) | Feed (g) | Output (g) | Pyrroline | Pyrrolidine (area-% in GC) | Pyrrole | Others | Conversion % | Sel. % |
|---|---|---|---|---|---|---|---|---|---|
| Catalyst B: | | | | | | | | | |
| 7 | 230 | 298 | 228 | 0.9 | 3.7 | 87.0 | 8.4 | 96.3 | 90.3 |
| 14 | 230 | 298 | 255 | 1.3 | 5.8 | 85.7 | 7.2 | 94.2 | 91.0 |
| 21 | 230 | 298 | 251 | 1.7 | 6.6 | 85.6 | 6.1 | 93.4 | 91.6 |
| 28 | 230 | 298 | 232 | 2.0 | 6.6 | 86.0 | 5.4 | 93.4 | 92.1 |
| 34 | 230 | 256 | 201 | 1.5 | 9.0 | 82.8 | 6.8 | 91.0 | 91.0 |
| Mean: | 230 | 290 | 233 | 1.5 ± 0.4 | 6.3 ± 1.9 | 85.4 ± 1.6 | 6.8 ± 1.1 | 93.7 ± 1.9 | 91.2 ± 0.7 |

It can be seen that the catalyst B gives significantly higher amounts of pyrrole at the same conversions. It is also significantly more active, which can be seen from the lower reaction temperature, and the operating life is greater.

We claim:

1. A process for preparing pyrroles of the formula I:

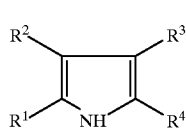

(I)

where $R^1$, $R^2$, $R^3$ and $R^4$ are identical or different and are hydrogen atoms, alkyl groups having from 1 to 12 carbon atoms or cycloalkyl groups having from 3 to 12 carbon atoms, by dehydrogenation of pyrrolidines of the formula II:

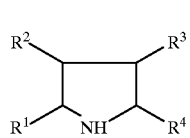

(II)

where $R^1$, $R^2$, $R^3$ and $R^4$ are as defined above, in the presence of a supported noble metal catalyst, wherein the dehydrogenation is carried out at from 150 to 300° C. and pressures of from 0.01 to 50 bar and the noble metal catalyst comprises from 30 to 100% by weight of:

a) palladium on an oxide of a rare earth or an oxide of an element of the $4^{th}$ group (transition group IV) of the Periodic Table, or b) a platinum/palladium mixture on aluminum oxide, an oxide of a rare earth or an oxide of an element of the $4^{th}$ group and from 0 to 70% by weight of alkali metal oxide or alkaline earth metal oxide.

2. A process as claimed in claim 1, wherein the reaction is carried out in the liquid phase or in the gas phase.

3. A process as claimed in claim 1, wherein the reaction is carried out in the presence of hydrogen in an amount of from 1 to 100 mol per mol of pyrrolidine.

4. A process as claimed in claim 1, wherein an oxide of cerium, praseodymium, neodymium, samarium, europium, terbium, ytterbium, thorium or protactinium is used as oxide of a rare earth.

5. A process as claimed in claim 1, wherein an oxide of titanium or zirconium is used as oxide of an element of the $4^{th}$ group.

6. A process as claimed in claim 1, wherein an oxide of sodium, potassium, magnesium, calcium or barium is used as alkali metal oxide or alkaline earth metal oxide.

7. A process as claimed in claim 1, wherein the noble metal content of the catalyst, based on the support material, is in the range from 0.0001 to 25% by weight.

8. A process as claimed in claim 1, wherein one of the radicals $R^1$, $R^2$, $R^3$ and $R^4$ is a hydrogen atom or a $C_1$–$C_4$-alkyl group and the others are hydrogen atoms.

* * * * *